United States Patent [19]

Agouridas et al.

[11] Patent Number: 5,296,501
[45] Date of Patent: Mar. 22, 1994

[54] 2,6-DIAMINO-HEPTANDEDIOIC ACIDS

[75] Inventors: Constantin Agouridas, Paris; Nicole Tessot, Claye-Souilly; Annie Martel, Fresnes, all of France

[73] Assignee: Roussel Uclaf, France

[21] Appl. No.: 53,464

[22] Filed: Apr. 27, 1993

Related U.S. Application Data

[63] Continuation of Ser. No. 848,265, Mar. 9, 1992, abandoned, which is a continuation of Ser. No. 509,552, Apr. 13, 1990, abandoned.

[30] Foreign Application Priority Data

Apr. 18, 1989 [FR] France .................. 89 05108

[51] Int. Cl.$^5$ ............... A61K 31/195; A61K 31/24; C07C 229/00
[52] U.S. Cl. ............... 514/566; 514/541; 562/565; 560/169
[58] Field of Search ............... 514/566, 541; 562/565; 560/169

[56] References Cited

PUBLICATIONS

Agouridas et al., Chem Abst., (Dec. 5, 1985), vol. 105, 173044g, "Diaminopimelic acid derivatives", (Fr. Dewande FR 2,566,410).
Givodeau et al., Chem Abst., (1986), vol. 104, 2076372, "The Lysine Pathway . . . ", (J. Med. Chem., 1986, 29(6), 1023–30).

Primary Examiner—Frederick E. Waddell
Assistant Examiner—Gregory Hook
Attorney, Agent, or Firm—Bierman and Muserlian

[57] ABSTRACT

A compound selected from the group consisting of a compound of the formula

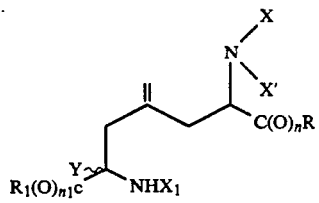

wherein the dotted lines indicate an optionally endo or exo double bond, Y is selected from the group consisting of alkyl, alkenyl and alkynyl of 2 to 18 carbon atoms and alkyl of 1 to 18 carbon atoms substituted with at least one halogen, X, X' and $X_1$ are individually selected from the group consisting of hydrogen, alkyl of 1 to 8 carbon atoms, alkenyl and alkynyl of 2 to 8 carbon atoms, aryl of 6 to 14 carbon atoms, aralkyl of 7 to 18 carbon atoms, acyl of a fatty acid and acyl of an α or ω-amino acid, n and/or $n_1$ is 1 and R and/or $R_1$ is the remainder of an amine or an α or ω-amino acid or n and/or $n_1$ is 2 and R and $R_1$ are selected from the group consisting of hydrogen, alkyl of 1 to 8 carbon atoms, aryl of 6 to 14 carbon atoms, aralkyl of 7 to 18 carbon atoms and

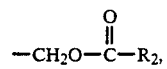

$R_2$ is alkyl of 1 to 8 carbon atoms or aryl of 6 to 14 carbon atoms and their non-toxic, pharmaceutically acceptable salts with acids or bases having antibacterial properties.

25 Claims, No Drawings

2,6-DIAMINO-HEPTANDEDIOIC ACIDS

PRIOR APPLICATION

This application is a continuation of U.S. patent application Ser. No. 848,265 filed Mar. 9, 1992, which is a continuation of U.S. patent application Ser. No. 509,552 filed Apr. 13, 1990, both now abandoned.

STATE OF THE ART

Related prior art includes French patents No. 2,566,410 and British patent No. 2,104,887, commonly assigned U.S. patent applications Ser. No. 161,163 filed Feb. 26, 1988, now U.S. Pat. 5,089,476, and Ser. No. 396,631 filed Aug. 21, 1989, now U.S. Pat. No. 5,108,990, as well as J. of Medicinal Chemistry, Vol. 29 No. 6 (1986), p. 1023 to 1030 and Tetrahedron Letters, Vol. 26 No. 26 (1985), p. 3115 to 3118.

OBJECTS OF THE INVENTION

It is an object of the invention to provide the novel compounds of formula I and their non-toxic, pharmaceutically acceptable addition salts and a novel process and intermediates for their properties.

It is another object of the invention to provide novel bactericidal compositions and a novel method of treating bacterial infections in warm-blooded animals.

These and other obects and advantages of the invention will become obvious from the following detailed description.

THE INVENTION

The novel compounds of the invention are selected from the group consisting of a compound of the formula

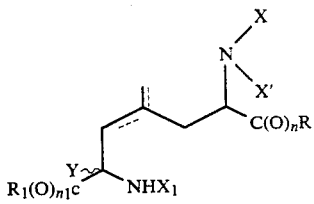

wherein the dotted lines indicate an optionally endo or exo double bond, Y is selected from the group consisting of alkyl, alkenyl and alkynyl of 2 to 18 carbon atoms and alkyl of 1 to 18 carbon atoms substituted with at least one halogen, X, X' and $X_1$ are individually selected from the group consisting of hydrogen, alkyl of 1 to 8 carbon atoms, alkenyl and alkynyl of 2 to 8 carbon atoms, aryl of 6 to 14 carbon atoms, aralkyl of 7 to 18 carbon atoms, acyl of a fatty acid and acyl of an α or ω-amino acid, n and/or $n_1$ is 1 and R and/or $R_1$ is the remainder of an amine or an α or ω-amino acid or n and/or $n_1$ is 2 and R and $R_1$ are selected from the group consisting of hydrogen, alkyl of 1 to 8 carbon atoms, aryl of 6 to 14 carbon atoms, aralkyl of 7 to 18 carbon atoms and

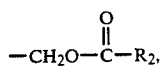

$R_2$ is alkyl of 1 to 8 carbon atoms or aryl of 6 to 14 carbon atoms and their non-toxic, pharmaceutically acceptable salts with acids or bases.

Examples of Y as alkyl are ethyl, propyl, isopropyl and butyl and an alkenyl or alkynyl are vinyl, allyl, propynyl or ethynyl. Examples of Y as haloalkyl or alkyl substituted with at least one chlorine or fluorine are such as $-CHF_2$, $-CH_2-CHCl_2$ and $-CH_2Cl$.

Examples of X, X', $X_1$, R, $R_1$ or $R_2$ as alkyl are methyl, ethyl, propyl, isopropyl, butyl or aryl or aralkyl are phenyl and benzyl. Examples of X, X' or $X_1$ as alkenyl or alkynyl are vinyl, allyl, ethynyl or propynyl, $R_2$ is preferably methyl, ethyl, n-propyl or phenyl.

Examples of fatty acids are saturated or unsaturated aliphatic acids of 6 to 24 carbon atoms, preferably 12 to 22 carbon atoms, such as stearic acid, palmitic acid, lauric acid, caprylic acid, myristic acid, α- or ω-linolenic acid, linoleic acid, arachidonic acid, docosapentaenoic acid or adamantane carboxylic acid. Examples of suitable amino groups are methylamine, dimethylamine and other secondary and tertiary amines.

Examples of suitable amino acid groups are [Ala, Val, Ival, Leu, Ile, Asp, Asn, Glu, Gln, Ser, Thr, Cys, Met, Lys, Arg, Phe, Tyr, Trp, His and Pro, Nva, Nle, Hyp, Orn, these acids being in the D or L form, and Sar and Gly], all the previously mentioned acids capable of being N-acylated or N-alkylated. By convention, it will be acknowledged that the symbols for the α-amino carboxylic acids represent these acids in their D or L configuration (for example, the term Ala signifies Alanine in the D form or in the L form).

Examples of suitable acids for the preparation of non-toxic, pharmaceutically acceptable acid addition salts are inorganic acids such as hydrochloric acid, hydrobromic acid, nitric acid, sulfuric acid and phosphoric acid, organic acids such as acetic acid, formic acid, propionic acid, maleic acid, fumaric acid, succinic acid, tartaric acid, citric acid, oxalic acid, glyoxylic acid, aspartic acid, alkanesulfonic acids, such as methane- or ethanesulfonic acid, arylsulfonic acids such as benzene- or p-toluenesulfonic acid or arylcarboxylic acids such as benzoic acid.

Examples of suitable bases for the formation of the salts are alkali metal hydroxides and alkaline earth metal hydroxides such as sodium hydroxide, the potassium hydroxide, lithium hydroxide, calcium hydroxide, magnesium hydroxide and ammonium hydroxide or organic bases such as substitued or non-substituted alkylamines such as methylamine, methyl propylamine N,N-diethylethanolamine, and tris(hydroxy methyl) methylamine or basic amino acids such as lysine or arginine as well as bases such as glucosamine or procaine.

Among the preferred compounds of formula I are those wherein the dotted lines are an exo double bond, those wherein X' is hydrogen, those wherein X, X' and $X_1$ are hydrogen, those wherein X' is hydrogen or $-CH_3$, X is $-CH_3$ or benzyl and $X_1$ is hydrogen, those wherein $X_1$ is hydrogen and R and $R_1$ are hydrogen, those wherein Y is acetylene or ethylene or ethyl and their non-toxic, pharmaceutically acceptable salts with acids and bases.

Specific preferred compounds of formula I are 2,6-diamino-2-ethyl-4-methylene-heptanedioic acid, 2,6-diamino-2-ethenyl-4-methylene-heptanedioic acid and 2-amino-2-ethynyl-4-methylene-6-benzylamino-heptanedioic acid.

The novel process of the invention for the preparation of a compound of formula I comprises reacting a compound of the formula

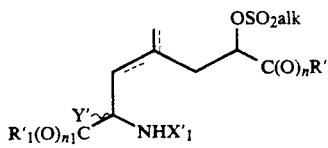    II wherein alk is alkyl of 1 to 8 carbon atoms optionally substituted with at least one halogen, n, $n_1$ and the dotted lines have the above definitions, Y' is Y or a precursor of Y, $X_1'$ R' and $R_1'$ have the definitions of X, R and $R_1$ respectively other than hydrogen with an amine of the formula

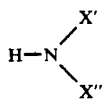

or a precursor thereof wherein X' has the above definition and X" has the definition of X other than hydrogen to obtain the compound of formula I which is optionally subjected to any of the following steps in any order; deprotection of the amine functions, functionalization of the amine functions, hydrolysis of the ester functions, the treatment of Y' to obtain Y, total or selective reduction of Y when it is unsaturated and salification.

In a preferred embodiment, alk is methyl, ethyl or n-propyl or $-CF_3$ and the reagent capable of providing a precursor of the amino function is sodium nitride, potassium phthalamide or hydroxylamine.

The amine is obtained by methods known to the expert, for example by hydrolysis in the case of phthalamide. The hydrolysis agent of phthalamide in this case can be a mineral base followed by an acid hydrolysis or hydrazine; the deprotection of the amine function is effected preferably by the action of a dilute mineral acid such as hydrochloric acid, or an organic acid such as trifluoroacetic acid; the hydrolysis of the ester functions is effected preferably by saponification using a mineral base such as sodium or potassium hydroxide, optionally followed by a treatment by an acid resin, and the salification is effected by the addition of an acid or base to the reaction medium.

In a variant of the process of the invention, a compound of formula II is subjected to the action of sodium nitride to obtain the compound of the formula

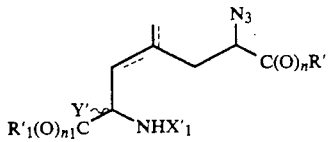    III which is subjected to a reducing agent of the $N_3$ group to obtain a compound of the formula

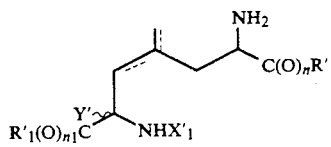    IV which is subjected either to all or part of the operations mentioned previously.

In a preferred embodiment, the reducing agent reacted with the compound of formula III is triphenyl phosphine, followed by an acid hydrolysis. Equally, the procedure can be catalytic hydrogenation, for example in the presence of palladium on activated charcoal poisoned by quinoline.

A more particular subject of the invention is a process comprising reacting a compound of the formula

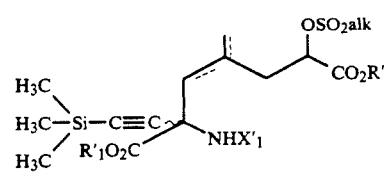    II$_A$ either with sodium nitride to obtain a compound of the formula

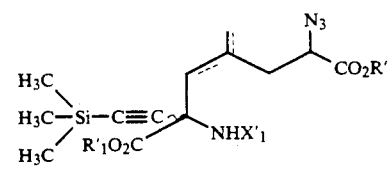    III$_A$ which is subjected to the action of a reducing agent of the nitride to obtain a compound of the formula

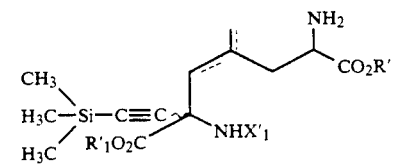    IV$_A$ or with an amine of the formula

in which X' and X" have the meaning indicated above to obtain a compound of the formula

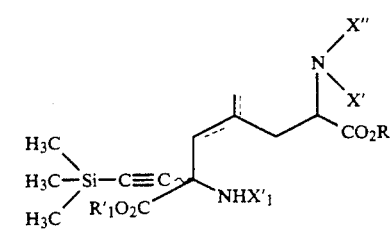    IV$_B$ then either the compound of formula IV$_A$ or IV$_B$ is subjected to the action of a selective cleaving agent of the ester functions and of the trimethylsilyl radical to obtain a compound of the formula

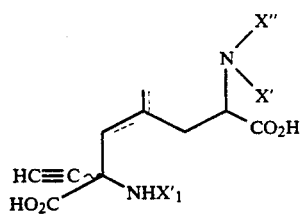

$I_A$ optionally subjecting the latter to the action of a cleaving agent of the amine protector group to obtain a compound of the formula

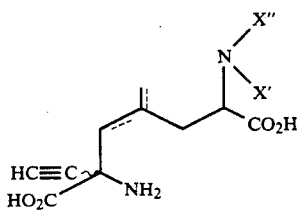

$I_B$ or the compound of formula $IV_A$ or $IV_B$ is subjected to the action of a cleaving agent of the trimethylsilyl to obtain a compound of the formula

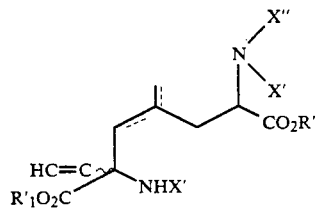

$I_C$ and optionally the compound of formula $I_A$, $I_B$ or $I_C$ is subjected to the action of a partial reducing agent to obtain the corresponding compound of formula $I_D$ in which Y is ethynyl or to the action of a total reducing agent of the triple bond to obtain the corresponding compound of formula $I_E$ in which Y is ethyl, then, if appropriate, the compounds of formula I thus obtained are subjected to all or part of the operations mentioned previously.

In a preferred embodiment of the process, the cleaving agent of the trimethylsilyl group is potassium fluoride or tetrabutylammonium fluoride.

The products of formula I in which R and/or $R_1$ are the remainder of an amine can be obtained by amidification of the acid functions of the product of formula $I_A$ wherein the amidification is effected in the presence of condensation agents such as dicyclohexylcarbodiimide, N,N'-carbonylidiimidazole, or the bis-alkyl amides of sulfurated acids such as N,N'-sulfinyl-bis(dimethylamine), $SO[N(CH_3)_3]_2$, or also by the formation of the mixed anhydride with isobutyl chloroformate.

Certain starting products of formula II are described in European Patent Application No. 88 402741.8 filed on Nov. 2, 1988 and their preparation is mentioned hereafter. The compounds of formula II and $II_A$ can be prepared, for example, by the processes described hereafter in the experimental part, for example, according to the scheme

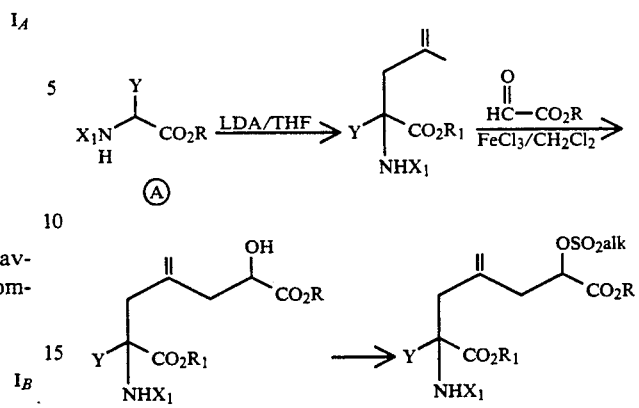

The compounds of formula II in which Y' is alkynyl trimethylsilyl and of formula III and $III_A$ are new and are themselves a subject of the invention.

The products A are known and can, for example, be prepared by the process described in U.S. Pat. No. 4,088,667 or in CASARA et al, Tet. Lett, (1978) p. 1581 and fol.

The novel antibacterial compositions of the invention are comprised of an antibactericidally effective amount of at least one compound of formula I and its non-toxic, pharmaceutically acceptable salts with acids and bases and an inert pharmaceutical carrier. The compositions may be in the form of tablets, dragees, capsules, granules suppositories and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions due their antibacterial activity are useful in antibiotherapy vis-a-vis bacterial germs, yeasts, fungi (candida albicans . . . ) in anti-viral therapy, and in anticancer chemotherapy, by themselves or in combination, and lastly as adjuvants to a standard antibiotherapy or to vaccination.

The novel method of the invention for treating bacterial infections in warm-blooded animals, including humans, comprises administering to warm-blooded animals an antibactericidally effective amount of at least one compound of formula I and its non-toxic, pharmaceutically acceptable salts with acids or bases. The compounds may be administered orally, rectally or parenterally and the usual daily dose is 0.26 to 2.66 mg/kg depending on the condition treated, the method of administration and the specific compound used.

In the following examples, there are described several preferred embodiments to illustrate the invention. However it should be understood that the invention is not intended to be limited to the specific embodiments.

EXAMPLE 1

6-amino-2-ethynyl-2-[methoxycarbonyl)-amino]-4-methyleneheptanedioc acid

STEP A:

7-ethyl-1-methyl-6-azido-2-[(methoxycarbonyl)-amino]-4-methylene-2-[2-(trimethylsilyl)-ethynyl]-heptanedioate 0.498 g of sodium nitride were added to a solution of 3.32 g of 7-ethyl-1-methyl-6-(methanesulfonyloxy)-2[(methoxycarbonyl)-amino-4-methylene-2-[2-[2-(trimethyl)-ethynyl]-heptanedioate prepared as indicated in preparation 1 and 30 ml of dimethylformamide and the reaction medium was stirred for 16 hours and was filtered and diluted with water. The mixture was extracted with ether and the extracts were dried and evaporated to dryness to obtain 3.7 g of the desired product which was purified by chromatography on silica eluting with a cyclohexanethyl acetate (6-4) mixture to obtain 2.28 g of the product with a Rf.=0.35.

STEP B:

7-ethyl-1-methyl-6-amino-2-[(methoxycarbonyl)-amino]-4-methylene-2-[2-trimethylsilyl)-ethynyl]-heptanedioate 519 mg of the product of Step A were dissolved in 6 ml of tetrahydrofuran and 341 mg of triphenyl-phosphine were added. The mixture was stirred for 16 hours at ambient temperature and 0.65 ml of water were added. The mixture was stirred for 30 hours and the product obtained was diluted with ether and extracted with a normal solution of hydrochloric acid. The aqueous phase was washed with ether and after sodium bicarbonate was added, extraction took place with ether, followed by washing, drying and evaporation to dryness to obtain 433 mg of the sought product with a Rf=0.4 (eluant ethyl acetate).

STEP C:

6-amino-2-ethynyl-2-[(methoxycarbonyl)-amino]-4-methylene heptanedioic acid 1.23 g of the product of Step B were dissolved in ml of ethanol and after the mixture was cooled to +4° C., 5 ml of a 2N solution of sodium hydroxide were added. The solution was allowed to rise to ambient temperature and stirred for 38 hours. 50 W×8 Dowex resin was added and the mixture was filtered, rinsed with water, diluted with dilute ammonium hydroxide and evaporated to dryness to obtain 709 mg of the product which was chromatographed on silica eluting with an ethanol-ammonium hydroxide mixture (8-2) to obtain 600 mg of the sought product with a Rf=0.2.

PREPARATION 1: 7-ethyl-1-methyl 6-(methanesulfonyloxy)-2-[(methoxycarbonyl)-amino]-4-methylene-2-[2-trimethylsilyl)ethynyl]-heptanedioate A solution of 183.4 g of diisopropylamine in 5570 ml of tetrahydrofuran was cooled to −60° C. and 1135 ml of 15% butyllithium in hexane were introduced at −50° C. and −60° C. The temperature was allowed to rise to 0° C. and stirred for 15 minutes, followed by cooling to −66° C./−65° C. A solution of 147 g of methyl 2-[(methoxycarbonyl)-amino]-4-(trimethylsilyl)-3-butynoate [prepared as indicated for the same ethyl carbonate in Tetrahedron Letters No. 18, p. 1581 (1978)], in 1100 ml of tetrahydrofuran was added over 50 minutes. The mixture was stirred for 45 minutes at −65° C./−70° C. and at this temperature, 558.6 ml of hexamethyl phosphotriamide were added. The mixture was stirred for 15 minutes at this temperature and 81.6 g of methallyl bromide in solution in 100 ml of tetrahydrofuran were added. The mixture was stirred for 2 hours at −67° C./−70° C. and 186 ml of acetic acid diluted 10 times in tetrahydrofuran were added. The temperature of the mixture was allowed to rise to +20° C. and was then filtered, washed with tetrahydrofuran and distilled to dryness under reduced pressure. The dry extract was taken up in methylene chloride and washed with water. The organic phases were dried, washed with methylene chloride and brought to dryness to obtain 587.5 g of crude product which was chromatographed on silica and eluted with a cyclohexane-ethyl acetate mixture (7-3) to obtain the sought product with a Rf=0.4.

STEP B: 7-ethyl-1-methyl 6-hydroxy-2-[methoxycarbonyl)-amino]-4-methylene-2-[2-(trimethylsilyl)-ethynyl]-heptanedioate 9.72 g of ferric chloride were suspended in 50 ml of methylene chloride in the presence of siliporite and the mixture was cooled to 0° C. 3.1 g of ethyl glyoxylate in solution in 40 ml of methylene chloride were introduced over 30 minutes and the mixture was stirred for 30 minutes at ambient temperature. The solution was cooled to −60° C. and 4.5 g of the product of Step A in solution in 40 ml of methylene chloride were introduced over 35 minutes. The reaction medium was stirred at −60° C. for 2 hours and was poured over an excess of sodium bicarbonate (the medium remaining basic), followed by filtering and rinsing. Washing with water, drying and evaporating to dryness yielded 6.4 g of product which was purified by chromatography on silica eluting with a cyclohexane-ethyl acetate mixture (5-5) to obtain 3.64 g of the sought product with a Rf=0.37.

STEP C: 7-ethyl-1-methyl 6-(methanesulfonyloxy)-2-[(methoxy-carbonyl)-amino]-4-methylene-2-[2-trimethylsilyl)-ethynyl]heptanedioate 8.43 g of the product of Step B in 70 ml of pyridine were cooled to 0° C. and 1.7 ml of mesyl chloride were introduced. The mixture was stirred for 5 hours at ambient temperature and the pyridine was evaporated off at ambient temperature under reduced pressure. The residue was taken up in ether and the ether solution was washed with a normal solution of hydrochloric acid until an acid pH was obtained, then washed with salt water until neutral. The organic phase was dried and evaporated to dryness at a temperature lower than 30° C. to obtain 11 g of product which was chromatographed by eluting with a cyclohexane-ethyl acetate mixture (6-4) to obtain 8.28 g of the desired product with a Rf=0.35.

EXAMPLE 2

2,6-diamino-2-ethynyl-4-methylene heptanedioic acid

A mixture of 246 mg of the product of Step B of Example 1 and 5 ml of 5N sodium hydroxide was heated for 5 hours at 120° C. and the mixture was ice-cooled, brought to pH 6 with concentrated hydrochloric acid and evaporated to dryness. The product was passed over an ion-exchange resin of 50 W×8 Dowex. Elution was carried out with water and then with a 2N ammonium hydroxide solution and the fractions containing the product were evaporated to dryness. After lyophilization, 85 mg of the desired product with a Rf.=0.24

(eluant: butanol-ethyl acetate-water (4-2-2)) were obtained.

EXAMPLE 3

6-amino-2-ethenyl-2-[(methoxycarbonyl)-amino]-4-methylene heptanedioic acid

STEP A: 7-ethyl-1-methyl 6-amino-2-ethynyl-2-[(methoxy-carbonyl)-amino]-4-methylene heptanedioate 99 mg of potassium fluoride were added to a solution of 338 mg of the product of Step B of Example 1 in 4 ml of dimethylformamide and the mixture was stirred at ambient temperature for 16 hours, then diluted with ether, washed with water, dried and evaporated to dryness to obtain 320 mg of product which was chromatographed on silica, eluting with a cyclohexane-ethyl acetate mixture (7-3) and then eluting with ethyl acetate to obtain 182 mg of the desired product with a Rf=0.3.

STEP B: 7-ethyl-1-methyl 6-amino-2-ethenyl-2-[(methoxy-carbonyl)-amino]-4-methylene heptanedioate 494 mg of the product of Step A were dissolved in 50 ml of ethanol and 99 microliters of quinoline and 250 mg of 5% palladium on barium sulfate were added. Hydrogenation (P=1200 mm/Hg) was carried out until absorption of 34 ml, followed by filtering, rinsing with ethanol and evaporating to dryness to obtain 560 mg of product which was purified by chromatography on silica and eluted with ethyl acetate to obtain 433 mg of the desired product with a Rf.=0.3.

STEP C: 6-amino-2-ethynyl-2-[(methoxycarbonyl)-amino-4-methylene heptanedioic acid 400 mg of the product of Step B were dissolved in 2.5 ml of ethanol and after the solution was ice-cooled, 2.5 ml of 2N sodium hydroxide were introduced. The mixture was stirred for 24 hours at ambient temperature and 1 ml of sodium hydroxide was added followed by stirring for 3 hours at ambient temperature. The solution was diluted with water and 50×8 Dowex resin was added until a pH of 2 was obtained. Filtration followed by rinsing with water, eluting with N ammonium hydroxide, then with 40% ammonium hydroxide, and evaporating to dryness yielded 208 mg of the desired product with a Rf.=0.25 (eluant: EtOH-NH4OH (8-2)).

EXAMPLE 4

2,6-diamino-2-ethenyl-4-methylene heptanedioic acid 220 mg of the product of Step C of Example 3 were dissolved in 2.5 ml of water and 2.5 ml of sodium hydroxide and the solution was heated at 100° C. for 5 hours and then allowed to return to ambient temperature. Ice was added and the mixture was acidified with 50 W×8 Dowex resin. Filtration was carried out followed by rinsing with water, then with dilute ammonium hydroxide, and evaporating to dryness to obtain 190 mg of product which was chromatographed on silica and eluted with an ethanol-ammonium hydroxide mixture (8-2) to obtain 76 mg of the desired product with a Rf.=0.5.

EXAMPLE 5

1-methyl 6-amino-2-ethyl-2-[(methoxycarbonyl)-amino]-4-methylene heptanediaote

STEP A: 7-ethyl-1-methyl 6-amino-2-ethyl-2-[(methoxycarbonyl)-amino]-4-methylene heptanedioate 1.17 g of the product of Step A of Example 3 were dissolved in 100 ml of ethanol and 1.1 g of 5% palladium on barium sulfate and 0.1 ml of quinoline were added. Hydrogenation was carried out until saturation was reached, followed by filtering, rinsing with ethanol and evaporating to dryness to obtain 1.32 g of product which was purified by chromatography on silica, eluting with ethyl acetate to obtain 1.1 g of the desired product with a Rf.=0.35.

STEP B: 1-methyl 6-amino-2-ethyl-2-[(methoxycarbonyl)-amino]-4-methylene heptanedioate 200 mg of the product of Step A were dissolved in 2 ml of ethanol and 0.55 ml of N sodium hydroxide was added dropwise at ambient temperature. The mixture was stirred at ambient temperature for 90 minutes, then diluted with water and acidified to a pH of 3 with 50 W 8 Dowex resin. Filtration was carried out followed by rinsing with water and the amino fraction was extracted by washing the resin with ammonium hydroxide diluted to one tenth. After evaporation to dryness, the residue was taken up in water, filtered and lyophilized to obtain 131 mg of product which was purified by chromatography on silica, eluting with a methylene chloride-methanol mixture (8-2). Rf=0.25. The product obtained was prepared by being passed over resin to obtain a 44% yield of the desired product.

EXAMPLE 6

6-amino-2-ethyl-2-[(methoxycarbonyl)-amino]-4-methylene heptanedioic acid 2.25 ml of 2N sodium hydroxide were introduced at 0° C. to a solution of 225 mg of the product of Step A of Example 5 in 2.25 ml of ethanol and the solution was allowed to return to ambient temperature, then stirred for 16 hours and diluted with water. 50 W×8 Dowex resin was added and after stirring for 30 minutes, filtration was carried out. The filtrate was rinsed with water and elution was done with one tenth ammonium hydroxide, followed by evaporation to dryness to obtain 180 mg of product which was purified by chromatography on silica, eluting with an ethanol-ammonium hydroxide mixture (8-2) to obtain the desired product with a Rf=0.6.

EXAMPLE 7

2,6-diamino-2-ethyl-4-methylene heptanedioic acid 300 mg of the product of Step A of Example 5 were dissolved in 3 ml of ethanol and 3 ml of sodium hydroxide were added to the solution. The mixture was held at 90° C. for 13 hours and ice was added. Acidification to pH 2 was carried out by adding 50 W×8 Dowex resin, followed by filtration and rinsing with water. Elution was done with dilute ammonium hydroxide followed by evaporation to dryness to obtain 230 mg of product which was purified by chromatography on silica, eluting with an ethanol-ammonium hydroxide mixture (8-2)

EXAMPLE 8

2,6-diamino-2-(difluoromethyl)-4-methylene heptanedioic acid

STEP A: Diethyl 6-azido-2-difluoromethyl-2-formyl-amino-4-methylene heptanedioate 0.131 g of sodium nitride were added to a solution of 0.700 g of diethyl 2-(difluoromethyl)-2-(formylamino)-4-methylene-6-[(methanesulfonyl)-oxy]-heptanedioate in 15 ml of dimethylformamide and the solution was stirred for 16 hours at ambient temperature. The dimethylformamide was evaporated off at 35° C. under reduced pressure and the residue was taken up in methylene chloride and washed with a 10% aqueous solution of sodium bicarbonate, then with brine, dried and evaporated to dryness to obtain 655 mg of desired product with a Rf.=0.65 (eluant: $CHCl_2$-AcOEt (8-2)).

STEP B: Diethyl 6-amino-2-difluoromethyl-2-formyl-amino-4-methylene heptanedioate 310 mg of triphenyl phosphine were added at 0° C. to a solution of 350 mg of the product of Step A and 20 ml of tetrahydrofuran. The solution was allowed to return to ambient temperature and was then stirred for 16 hours. 0.5 ml of water were added and the reaction mixture was stirred for 24 hours. The tetrahydrofuran was evaporated and the residue was taken up in methylene chloride. Extraction was done with a 2N hydrochloric acid solution, followed by neutralizing with a solution of sodium bicarbonate, and extraction with ethyl acotate. The extracts were washed, dried and evaporated to dryness to obtain 250 mg of the desired product with a Rf.=0.15.

STEP C: 2,6-diamino-2-(difluoromethyl)-4-methylene heptanedioic acid a) De-formylation

A solution of 140 mg of the product of Step B in 5 ml of ethanol and 0.5 ml of 12N hydrochloric acid was refluxed for one hour and then neutralized with sodium bicarbonate and evaporated to dryness. The residue was taken up in water and extraction was done with ethyl acetate. The extract were washed with water, dried and evaporated to dryness to obtain 100 mg of the product.

b) Saponification

The product of Step a) was taken up in 3 ml of ethanol and 1.5 ml of an N solution of sodium hydroxide were added. The reaction mixture was stirred for 16 hours at ambient temperature and then neutralized with a solution of hydrochloric acid to a pH of about 5. After evaporation to dryness, the residue was taken up in water. The product was placed on an ion-exchange resin (50 W×8 Dowex) and elution was done with water, then with a 0.7N solution of ammonium hydroxide. After reuniting, the fractions containing the desired product were evaporated to dryness to obtain 80 ml of the desired product which was lyophilized and had a Rf=0.25 in BuOH, AcOH, $H_2O$ (4-2-2).

PREPARATION 2: Diethyl 2-(difluoromethyl)-2-formylamino-4-methylene 6-[(methylsulfonyl)-oxy]-heptanedioate

STEP A: (1) (1,1-dimethylethyl) (3) ethyl (2-methyl-2-propenyl) propanedioate 33 g of ethyl tertbutyl malonate were dissolved in 400 ml of acetonitrile and 29 g of potassium carbonate, 0.5 g of crown ether (18-6) and 300 g of 3-chloro-2-methyl-1-propene were added with stirring. The mixture was stirred for 16 hours at 65° C. and the insoluble part was filtered off. The filtrate was evaporated to dryness and the residue was chromatographed on silica, eluting with a cyclohexane-ethyl acetate mixture (95-5) to obtain 18 g of pure product and 22 g of a mixture. The mixture was chromatographed on silica, eluting with a cyclohexane-ethyl acetate mixture (97.5-2.5) to obtain a further 11 g of the product with a Rf=0.35 in cyclohexane-ethyl acetate (95-5).

STEP B: (1) (1,1-dimethylethyl) (3) ethyl (difluoromethyl) (2-methyl-2-propenyl)-propanedioate 2.8 g of sodium hydride were suspended in 100 ml of tetrahydrofuran and 11.1 g of the product of Step A in 100 ml of tetrahydrofuran were added dropwise. The mixture was stirred for one hour at 42° C. and Freon 22 hours was bubbled through for 15 minutes while stirring at 45° C. Stirring was continued for one hour at 45° C. and for one hour at ambient temperature under a Freon 22 atmosphere. The reaction medium was hydrolyzed with salt water and extracted with methylene chloride. The organic phase was washed with salt water, dried and concentrated to dryness to obtain 13 g of the expected product with a Rf=0.4 in cyclohexane-ethyl acetate (95-5).

STEP C: Monoethyl (difluoromethyl) (2-methyl-2-propenyl)propanedioate 13 g of the product of Step B were dissolved in 100 ml of methylene chloride and 70 ml of trifluoroacetic acid were added. The mixture was stirred for 90 minutes at ambient temperature and after concentrating to dryness under reduced pressure, the residue was taken up in methylene chloride and extracted with a 10% aqueous solution of sodium bicarbonate. The aqueous phase was washed with methylene chloride and neutralized with concentrated hydrochloric acid. Extraction was done with methylene chloride and the extracts were washed with salt water, dried and concentrated to dryness to obtain 5.3 g of the expected product with a Rf.=0.5 in $CH_2Cl_2$—MeOH—AcOH (9-0.5-0.5).

STEP D: Ethyl 2-(difluoromethyl)-2-(formylamino)-4-methyl-4-pentenoate 10.5 g of the product of Step C in 60 ml of thienyl chloride were stirred and refluxed for 3 hours. After evaporating to dryness, the residue was taken up in toluene and dried under reduced pressure to obtain 10.5 g of acid chloride. The latter was dissolved in 50 ml of acetone cooled to 0° C., and a solution of 3.35 g of sodium nitride in 20 ml of water was added dropwise, followed by stirring for one hour at 0° C. The acetone was evaporated off and extraction was done with ether. The extracts were washed with salt water, dried and evaporated to dryness to obtain 10 g of nitride. The latter was dissolved in 100 ml of formic acid and refluxed for 90 minutes, then allowed to return to ambient temperature. 40 ml of acetic anhydride were added dropwise with stirring for 3 hours at ambient temperature. 40 ml of ice-cooled water were added slowly, followed by evaporation to dryness. The residue was taken up in a water-methylene chloride mixture and extracted with methylene chloride. The extracts were washed with a 10% aqueous solution of sodium bicarbonate, then with salt water, dried and concentrated to dryness. The residue was chromatographed on silica, eluting with a cyclohexane-ethyl acetate mixture (85-15) to obtain 5 g of the expected product.

STEP E: Diethyl 2-(fluoromethyl)-2-(formylamino)-6-hydroxy-4-methylene heptanedioate 9.65 g of ferric chloride were suspended in 50 ml of methylene chloride and 3.03 g of ethyl glyoxylate in 50 ml of methylene chloride were added dropwise. Stirring was carried out for 30 minutes at ambient temperature and the mixture was cooled to −60° C. 3.5 g of the product of Step D in 50 ml of methylene chloride were added dropwise followed by stirring for one hour at −30° C. and then for one hour at −20° C. The reaction mixture was poured into ice-cooled water and extracted with methylene chloride. The extracts were washed with salt water, then with a 10% aqueous solution of sodium bicarbonate, then with salt water, dried and evaporated to dryness. The residue was chromatographed on silica, eluting with a cyclohexane-ethyl acetate mixture (6-4) to obtain 0.590 g of product B (4-methyl heptene...) and 1.7 g of product C (4-methylene heptane...) and 1 g of a mixture. Product B had a Rf=0.32 and Product C had a Rf=0.35 in cyclohexane-ethyl acetate (1-1)

STEP F: Diethyl 2-(difluoromethyl)-2-(formylamino)-4-methylene -6-[(methylsulfonyl)-oxy]-heptanedioate 1.65 g of product C of Step E were dissolved in 20 ml of pyridine cooled to 0° C. and 0.725 g of methane-sulfonyl chloride were added. The mixture was stirred for 30 minutes at 0° C. and for 5 hours at ambient temperature. The reaction mixture was poured into ice-cooled 6N hydrochloric acid and extracted with methylene chloride. The organic phase was washed with 6N hydrochloric acid and then with a 10% aqueous solution of sodium bicarbonate and finally with salt water, dried and evaporated to dryness. The residue was chromatographed on silica, eluting with a methylene chloride-ethyl acetate mixture (9-1) to obtain 1.55 g of the expected product with a Rf.=0.45 in $CH_2Cl_2$-AcOEt (8-2)

EXAMPLE 9

2-ethynyl-2-[(methoxycarbonyl)-amino]-4-methylene-6-[(phenylmethyl)-amino]-heptanedioic acid

STEP A: 7-methyl-1-methyl 2-[(methoxycarbonyl)-amino]-4-methylene-6-[(phenylmethyl)-amino]-2-[2-(trimethylsilyl)-ethynyl]heptanedioate A solution of 1.6 g of the product of preparation 3 in 40 ml of methylene chloride was added to a solution of 387 mg of triethylamine and 393 mg of benzylamine in 80 ml of methylene chloride. The mixture was stirred for 6 hours at ambient temperature, washed with a solution of N hydrochloric acid, then with a solution of sodium bicarbonate, dried and evaporated to dryness to obtain 1.54 g of crude desired product which was purified by chromatography on silica, eluting with a methylene chloride-ethyl acetate mixture (95-5) to obtain 1.2 g of the desired product with a Rf=0.28 ($CH_2Cl_2$, AcOEt (9-1)).

STEP B: 7-ethyl-1-methyl-2-ethynyl-2-[(methoxycarbonyl)-amino]-4-methylene-6-[benzyl-amino]-heptanedioate 0.23 g of potassium fluoride were added to 1.23 g of the product of Step A in solution in 30 ml of dimethylformamide and the mixture was stirred for 16 hours at ambient temperature, then diluted in 200 ml of ethyl ether. Washing, drying and evaporation to dryness were carried out to obtain 1.02 g of the desired product with a Rf=0.6 (cyclohexane-ethyl acetate (7-3)).

STEP C: 2-ethynyl-2-[methoxycarbonyl)-amino]-4-methylene-6-[(benzyl)-amino]-heptanedioic acid 0.5 ml of 2N sodium hydroxide were added to a solution of 140 mg of the product of Step B and 15 ml of ethanol and the mixture was stirred at ambient temperature for 3 days, then neutralized with 50 W×8 Dowex resin and filtered. The filtrate was washed with water, then eluted with 100 ml of 0.5N ammonium hydroxide. After evaporating to dryness, the residue was taken up in water, filtered and lyophilized to obtain 106 mg of the desired product with a Rf=0.25 (EtOH, $NH_4OH$ (9-1)).

PREPARATION 3: 7-ethyl-1-methyl 2-[-(methoxycarbonyl)-amino]-4-methylene-6-[-[(trifluoromethylsulfonyl)-oxy]-2-[2-(trimethylsilyl) ethynyl]-heptanedioate 1.015 g of trifluoromethane sulfonic anhydride were added at 0° C. to a solution of 594 mg of pyridine and 6 ml of methylene chloride and the solution was stirred for 10 minutes at 0° C. The solution was poured into a solution of 1.2 g of the product of Step B of preparation 1 in solution in 30 ml of methylene chloride. The mixture was stirred for 15 minutes at 0° C. and washing was carried out with N hydrochloric acid, then with a solution of sodium bicarbonate, followed by drying and evaporation to dryness at 30° C. to obtain 1.6 g of the desired product with a Rf=0.45 (cyclohexane-ethyl acetate (7-3)).

EXAMPLE 10

2-amino-2-ethynyl-4-methylene-6-[(phenylmethyl)-amino]-heptanedioic acid

A solution of 400 mg of the product of Example 9 in 35 ml of 6N sodium hydroxide was heated for 2 hours 30 minutes at 90° C. and the solution was neutralized with 12N hydrochloric acid until a pH of about 5 was obtained. After partial concentration, it was placed on 50 W×8 Dowex resin. After rinsing with water and eluting with 0.5N ammonium hydroxide, the fractions containing the product were reunited and evaporated to dryness to obtain 320 mg of product which was purified on silica, eluting with a methylene chloride-methanol-acetic acid mixture (5-4-1) to obtain 150 mg of product which was purified again by hromatography on silica, eluting with a $CH_2Cl_2$—MeOH—$H_2O$ mixture (5-5-2), then with a $CH_2Cl_2$—MeOH—$N_4OH$ mixture (5-5 -1) to obtain the desired pure product which was lyophilized and had a Rf.=0.35 (eluant: MeOH—AcO-H—H$_2$O (4-2-2)).

EXAMPLE 11
2-amino-6-(dimethylamino)-2-ethynyl-4-methylene heptanedioic acid

STEP A: 7-ethyl-1-methyl 2-[(methoxycarbonyl)-amino]-6-(dimethylamino)-4-methylene-2-(2-trimethylsily)-ethynyl]-heptanedioate 1.44 g of 7-ethyl-1-methyl 2-[(methoxycarbonyl)-amino]-4-methylene-6-[(trifluoromethylsulfonyl)-oxy]-2-[2-(trimethyl-silyl)-ethynyl heptanedioate prepared as in preparation 3 in 40 ml of tetrahydrofuran was cooled to 0° C. and dimethylamine was bubbled through for 5 minutes, followed by stirring for 30 minutes at 0° C. The solvent was evaporated off and the residue was taken up in methylene chloride, washed with a 10% aqueous solution of sodium bicarbonate and concentrated to dryness to obtain 1.2 g of crude product which was purified by choromatography on silica (eluant: methylene chloride-ethyl acetate 6-4) to obtain 440 mg of the expected product with a Rf.=0.33 (methylene chloride-ethyl acetate 6-4).

STEP B: 2-amino-6-(dimethylamino)-2-ethynyl-4-methylene heptanedioic acid 108 mg of potassium fluoride were added to 400 mg of the product of Step A in solution in 15 ml of dimethylformamide and the mixture was stirred for 16 hours at ambient temperature. After concentration to dryness, the residue was taken up in methylene chloride, washed with salt water, and the solvents were dried and evaporated to dryness to obtain 330 mg of 2-ethynyl intermediate. 300 mg of this product were dissolved in 10 ml of ethanol and 1.7 ml of 2N sodium hydroxide were added followed by stirring for 16 hours at ambient temperature. The solvent was evaporated off and the residue was taken up in 4 ml of 6N sodium hydroxide followed by stirring for 4 hours at 90° C. Neutralization was effected by treatment on Dowex resin for one hour and filtration was carried out. The filtrate was washed with water, then with 0.5N ammonium hydroxide to obtain 270 mg of crude product which was chromatographed on silica (eluant: ethanol-ammonium hydroxide 9-1, 8-2 then 7-3). Treatment was carried out again on Dowex resin, followed by elution with 0.5N ammonium hydroxide, and the residue was taken up in 10 ml of water and lyophilized to obtain 135 mg of expected product with a Rf.=0.25 (ethanol-ammonium hydroxide 8-20 then 7-3). Treatment was carried out again on Dowex resin, followed by elution with 0.5N ammonium hydroxide, and the residue was taken up in 10 ml of water and lyophilized to obtain 135 mg of expected product with a Rf.=0.25 (ethanol-ammonium hydroxide 8-2).

EXAMPLE 12
2-ethynyl-2-[(methoxycarbonyl)-amino]-4-methylene-6-(methyl-amino)-heptanedioic acid

STEP A: 7-ethyl-1-methyl 2-[(methoxycarbonyl)-amino]-6-methylamino)-4-methylene-2-[2-(trimethylsilyl)-ethynyl]-heptanedioate 1.4 ml of methylamine in ethanol solution (8.06M/l.) were added to a solution of 0.96 g of 7-ethyl-1-methyl 2-[(methoxycarbonyl)-amino]-4-methylene-6-[(trifluoromethyl-sulfonyl)-oxy]-2-[2-(trimethylsilyl)-ethynyl]-heptanedioate prepared as in preparation 3 in 25 ml of tetrahydrofuran, and the mixture was stirred for 15 minutes at ambient temperature. The solvent was evaporated off and the residue was taken up in methylene chloride, washed with a 10% aqueous solution of sodium bicarbonate, dried and concentrated to dryness to obtain 770 mg of product. The latter was chromatographed on silica (eluant:methylene chloride-ethyl acetate 6-4) to obtain 530 mg of the expected product with a Rf.=0.15 (methylene chloride-ethyl acetate 6-4).

STEP B: 7-ethyl-1-methyl 2-ethynyl-2-[(methoxycarbonyl)-amino]-6-(methylamino)-4-methylene heptanedioate Using the procedure of Step B of Example 9, 850 mg of the product of Step A in 30 ml of dimethylformamide and 260 mg of potassium fluoride were reacted to obtain 620 mg of the expected product with a Rf.=0.5 (methylene chloride-ethyl acetate 5-5).

STEP C: 2-ethynyl-2-[(methoxycarbonyl)-amino]-4-methylene-6-(methylamino)-heptanedioic acid Using the procedure of Step C of Example 9, 200 mg of the product of Step B in 15 ml of ethanol and 0.9 ml of 2N sodium hydroxide were reacted to obtain 156 mg of the expected product with a Rf.=0.3 (ethanol-ammonium hydroxide 8-2).

EXAMPLE 13
2-amino-6-(methylamino)-2-ethynyl-4-methylene heptanedioic acid A solution of 320 mg of the product of Example 12 in 35 ml of 6N sodium hydroxide was heated for 3 hours at 90° C. and the solution was washed with 12N hydrochloric acid until a pH of 3 is obtained, then treated on 50 W×8 Dowex resin, rinsed with water and eluted with 0.5N ammonium hydroxide. Then the fractions containing the product were reunited to obtain 220 mg of product which was purified on silica (eluant: ethanol-ammonium hydroxide 95-5, 90-10 then 85-15). After another treatment on Amberlyst 15 resin, washing with water, eluting with 0.5N ammonium hydroxide and lyophilizing, 53 mg of the expected pure product with a Rf.=0.2 (ethanol-ammonium hydroxide 85-15) were obtained.

EXAMPLE 14

Tablets were prepared containing 50 mg of the product of Example 2 and sufficient excipient of lactose, starch, talc and magnesium stearate for a tablet weighing 250 mg.

EXAMPLE 15

Capsules were prepared containing 100 mg of the product of Example 3 and sufficient standard excipient for capsules.

Anti-bacterial activity (in vitro)

The anti-bacterial activity of the products was determined by the method of diffusion in Davis Mingioli medium containing 1% of agar. The geloses used were poured into Petri dishes at 48° C., after sowing with 5×10$^{-5}$ germs/ml with the control bacterial strain. The inoculations came from a preculture of 24 hours in Davis Mingioli medium. After hardening of the geloses, the aqueous solutions of the products studied were introduced into the wells (9 mm) hollowed into the medium with a punch. The areas of inhibition observed (diameter in mm) were measured after incubation for 24 hours at 37° C. and the results are in the following Table.

|  | Product of Example 4 (100 mg/l) | Product of Example 7 (100 mg/l) | Product of Example 10 (100 mg/l) |
|---|---|---|---|
| *Escherichia Coli* 078 | 17.5 | 18 | |
| *Salmonella typhimurium* MZ11 | 31 | 34 | 19 |
| *Enterobacter cloacae* 1321E | 26 | 29 | |
| *Providencia* sp. DU48 | 29 | 28 | |

Various modifications of the products and method of the invention may be made without departing from the spirit or scope thereof and it is to be understood that the invention is intended to be limited only as defined in the appended claims.

What we claim is:

1. A compound selected from the group consisting of a compound of formula

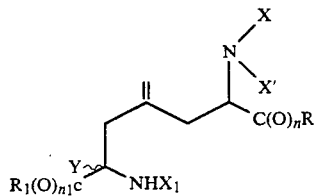

wherein Y is selected from the group consisting of alkenyl and alkynyl of 2 to 18 carbon atoms, X, X' and $X_1$ are individually selected from the group consisting of hydrogen, alkyl of 1 to 8 carbon atoms, alkenyl and alkynyl of 2 to 8 carbon atoms, aryl of 6 to 14 carbon atoms, aralkyl of 7 to 18 carbon atoms, or $n_1$ is 2 and R and $R_1$ are selected from the group consisting of hydrogen, alkyl of 1 to 8 carbon atoms, aryl of 6 to 14 carbon atoms, aralkyl of 7 to 18 carbon atoms and

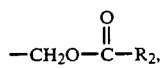

$R_2$ is alkyl of 1 to 8 carbon atoms or aryl of 6 to 14 carbon atoms and their non-toxic, pharmaceutically acceptable salts with acids or bases.

2. A compound of claim 1 wherein X is hydrogen.
3. A compound of claim 1 wherein X X' and $X_1$ are hydrogen.
4. A compound of claim 1 wherein X is hydrogen, X' is hydrogen or methyl and X is methyl or benzyl.
5. A compound of claim 1 wherein R and $R_1$ are hydrogen.
6. A compound of claim 1 wherein Y is acetylene.
7. A compound of claim 1 wherein Y is ethylene.
8. A compound of claim 1 selected from the group consisting of 2,6-diamino-2-ethenyl-4-methylene heptanedioic acid, and 2-amino-2-ethynyl-4-methylene-6-(phenylmethyl)-amino heptanedioic acid.
9. An antibacterial composition comprising an antibactericidally effective amount of at least one compound of claim 1 and an inert pharmaceutical carrier.
10. A composition of claim 9 wherein in the compound of claim 1 X' is hydrogen.
11. A composition of claim 9 wherein in the compound of claim 1 X, X' and $X_1$ are hydrogen.
12. A composition of claim 9 wherein in the compound of claim 1 X is hydrogen, X' is hydrogen or methyl and X is methyl or benzyl.
13. A composition of claim 9 wherein in the compound of claim 1 R and $R_1$ are hydrogen.
14. A composition of claim 9 wherein in the compound of claim 1 Y is acetylene.
15. A composition of claim 9 wherein in the compound of claim 1 Y is ethylene.
16. A composition of claim 9 wherein the active compound is selected from the group consisting of 2,6-diamino-2-ethenyl-4-methylene heptanedioic acid, and 2-amino-2-ethynyl-4-methylene-6-(phenylmethyl)-amino heptanedioic acid.
17. A method of combatting bacterial infections in warm-blooded animals comprising administering to warm-blooded animals an antibacterially effective amount of at least one compound of claim 1.
18. A method of claim 17 wherein in the compound of claim 1 the dotted lines are an exo double bond.
19. A method of claim 17 wherein in the compound of claim 1 X' is hydrogen.
20. A method of claim 17 wherein in the compound of claim 1 X, X' and $X_1$ are hydrogen.
21. A method of claim 17 wherein in the compound of claim 1 X is hydrogen, X' is hydrogen or methyl and X is methyl or benzyl.
22. A method of claim 17 wherein in the compound of claim 1 R and $R_1$ are hydrogen.
23. A method of claim 17 wherein in the compound of claim 1 Y is acetylene.
24. A method of claim 17 wherein in the compound of claim 1 Y is ethylene.
25. A method of claim 17 wherein the active compound is selected from the group consisting of 2,6-diamino-2-ethenyl-4-methylene heptanedioic acid, and 2-amino-2-ethynyl-4-methylene-6-(phenylmethyl)-amino heptanedioic acid.

* * * * *